(12) United States Patent
Ebenbeck et al.

(10) Patent No.: US 7,196,226 B2
(45) Date of Patent: Mar. 27, 2007

(54) FLUORAMINOOLEFINS AND FLUORINATION REAGENTS WHICH CAN BE PREPARED THEREFROM

(75) Inventors: Wolfgang Ebenbeck, Leverkusen (DE); Albrecht Marhold, Leverkusen (DE)

(73) Assignee: Lanxess Deutschland GmbH, Leverkusen (DE)

( * ) Notice: Subject to any disclaimer, the term of this patent is extended or adjusted under 35 U.S.C. 154(b) by 208 days.

(21) Appl. No.: 11/014,355

(22) Filed: Dec. 16, 2004

(65) Prior Publication Data
US 2005/0187412 A1    Aug. 25, 2005

(30) Foreign Application Priority Data
Dec. 18, 2003    (DE) ............... 103 59 629

(51) Int. Cl.
*C07C 211/21*    (2006.01)
(52) U.S. Cl. ............ 564/452; 564/319; 564/366; 564/412; 564/453; 564/454; 564/462; 564/496; 564/509
(58) Field of Classification Search ............ None
See application file for complete search history.

(56) References Cited

U.S. PATENT DOCUMENTS

| | | | |
|---|---|---|---|
| 3,976,691 A | 8/1976 | Middleton | 260/544 F |
| 4,497,937 A | 2/1985 | van der Klooster et al. | 525/333.1 |
| 5,218,097 A | 6/1993 | Ernst | 538/18.5 |
| 6,080,886 A | 6/2000 | Lal et al. | 560/227 |
| 6,222,064 B1 | 4/2001 | Lal et al. | 560/227 |
| 6,329,529 B1 | 12/2001 | Sonoda et al. | 548/300.1 |
| 6,458,990 B1 | 10/2002 | Sonoda et al. | 560/219 |
| 6,632,949 B2 | 10/2003 | Sonoda et al. | 548/300.1 |
| 2002/0042521 A1 | 4/2002 | Sonada et al. | 548/300.1 |
| 2003/0004348 A1 | 1/2003 | Sonoda et al. | 544/334 |

FOREIGN PATENT DOCUMENTS

WO    03/101921 A1 * 12/2003

OTHER PUBLICATIONS

Organic Synthesis, Bd. 59, 1979, Seiten 26-34, XP009046416, L. Ghosez et al: "Alpha-chloro enamines, reactive intermediates for synthesis: 1-chloro-N,N,2-trimethylpropenylamine".
J. Chem. Soc. Chem. Comm., 1979, Seiten 1180-1181, XP009046410, L. Ghosez et al, "Synthesis of acyl halides under very mild conditions".
Falbe J. Ed—Houben-Weyl (Herausgerber E Muller): "Carbonsäuren und Carbonsäure-Derivate" Carbonsaeuren und Carbonsaeure-Derivate, Methoden der Organischen Chemie, Stuttgart, G. Thieme Verlag, De, Bd. Teil 1 Band E 5, 1985, Seiten 593-600, XP002226389.
John Wiley & Sons, Inc., USA, ISBN: 0-471-19622-3, vol. 21, p. 158-159, 1974, "Organic Reactions" XP002325124.
J. Fluorine Chem., 42, 1989, pp. 137-143, P. A. Messina et al, "Aminosulfur Trifluorides: Relative Thermal Stability (1)".
J. Fluorine Chem., 23, 1983, pp. 219-228, W. Dmowski et al, "Dialkyl-α,α-Difluorobenzylamines and Dialkyl (Trifuloromethyl)-Amines—Novel Fluorinating Reagents".

* cited by examiner

*Primary Examiner*—Brian Davis
(74) *Attorney, Agent, or Firm*—Michael A. Miller

(57) ABSTRACT

The present invention relates to fluorination reagents comprising 1-fluoro-1-aminoolefins and also processes for preparing fluorination reagents comprising 1-fluoro-1-aminoolefins.

13 Claims, No Drawings

FLUORAMINOOLEFINS AND FLUORINATION REAGENTS WHICH CAN BE PREPARED THEREFROM

The present invention relates to fluorination reagents comprising 1-fluoro-1-aminoolefins and also processes for preparing fluorination reagents comprising 1-fluoro-1-aminoolefins.

Reagents known for the fluorination of alcohols or carbonyl compounds such as, in particular, ketones, carboxylic acids and aldehydes are, for example, sulphur tetrafluoride, diethylaminosulphur trifluoride (DAST) and bis(methoxyethyl)aminosulphur trifluoride (methoxy-DAST) (see also U.S. Pat. No. 3,976,691, EP-A 90 448 and EP-A 905 109). Disadvantages of the industrial use of sulphur tetrafluoride are its extremely high toxicity and the need for comprehensive safety issues; in addition, the aminosulphur trifluorides mentioned are shock-sensitive (J. Fluorine Chem. 1989, 42, 137) and are, owing to their explosive nature, subject to strict legal regulations.

A further reagent for the fluorination of secondary alcohols and carboxylic acids is N,N-dimethyl-1,1-difluorobenzylamine which is obtainable by reaction of N,N-dimethylbenzamide with sulphur tetrafluoride at 150° C. (J. Fluorine Chem., 1983, 23, 219–228). However, the reagent is restricted in terms of its range of usability and gives only moderate yields.

Furthermore, 2-chloro-1,1,2-trifluorotriethylamine, known as the Yarovenko reagent, is known as fluorinating agent for alcohol (Org. React. 1974, 21, 158). However, the reagent is not storage-stable and its preparation is very complicated.

A similar reagent, which is known under the name Ishikawa reagent, consists of a mixture of hexafluoropropyldialkylamine and pentafluoroalkenyldialkylamine, but this has the same disadvantages as mentioned above.

EP-A 895 991 discloses difluoromethylene-α,α-diazo compounds which can be used for fluorinating hydroxyl and carboxyl functions. However, owing to their high sensitivity to air and moisture, they have only limited suitability for industrial use.

There is therefore a need to provide fluorinating reagents which can be prepared efficiently from readily available starting materials, are storage-stable and can fluorinate hydroxyl and keto functions in good yields.

We have now found mixtures comprising compounds of the formula (I),

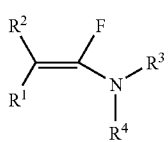

(I)

where
$R^1$ and $R^2$ are each, independently of one another, $C_1$–$C_{12}$-alkyl, $C_1$–$C_{12}$-fluoroalkyl, $C_4$–$C_{15}$-aryl, $C_5$–$C_{16}$-arylalkyl, or $[(C_2$–$C_{12}$-alkylene)-O]$_n(C_1$–$C_{12}$-alkyl)]$ where n=1 to 5 or are together part of a cyclic radical having a total of from 3 to 24 carbon atoms and
$R^3$ and $R^4$ are each, independently of one another, $C_1$–$C_{12}$-alkyl, $C_4$–$C_{15}$-arylalkyl or $C_5$–$C_{16}$-aryl or the moiety $NR^3R^4$ is a cyclic amino radical having a total of from 3 to 18 carbon atoms or $R^1$ and/or $R^2$ and $R^3$ and/or $R^4$ are together part of a cyclic radical having a total of from 4 to 18 carbon atoms,
at least one, preferably precisely one, aprotic, tertiary amine which has no fluorine atoms in the α-position relative to the nitrogen and/or at least one, preferably precisely one, N-heteroaromatic compound and
hydrogen fluoride.

In this context, aprotic means that the tertiary amine, which can also be a molecule having a plurality of tertiary amino groups, bears no hydrogen atoms which have a pKa of less than 20 based on an aqueous comparative scale at 25° C.

It may be remarked that the corresponding tertiary ammonia fluoride and N-heteroarylium fluoride and the corresponding polyfluorides as occurred in the reaction of hydrogen fluoride are also included under the concepts selected above for reasons of simplicity.

The scope of the invention also encompasses combinations of all radical definitions and parameters mentioned in general terms or in preferred ranges, i.e. including any combinations of the respective ranges and preferred ranges.

Alkyl or alkylene or alkoxy are in each case a straight-chain, cyclic, branched or unbranched alkyl or alkylene or alkoxy radical. The same applies to the nonaromatic part of an arylalkyl radical.

$C_1$–$C_4$-Alkyl is, for example, methyl, ethyl, n-propyl, isopropyl, n-butyl, sec-butyl and tert-butyl, $C_1$–$C_8$-alkyl can additionally be, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, $C_1$–$C_{12}$-alkyl can additionally be, for example, adamantyl, the isomeric menthyls, n-nonyl, n-decyl and n-dodecyl.

$C_1$–$C_4$-Alkoxy is, for example, methoxy, ethoxy, n-propoxy, isopropoxy, n-butoxy, sec-butoxy and tert-butoxy, $C_1$–$C_8$-alkoxy can additionally be n-pentoxy, 1-methylbutoxy, 2-methylbutoxy, 3-methylbutoxy, neopentoxy, 1-ethylpropoxy, cyclohexoxy, cyclopentoxy, n-hexoxy and n-octoxy, $C_1$–$C_{12}$-alkoxy can additionally be, for example, adamantoxy, the isomeric menthoxy radicals, n-decoxy and n-dodecoxy.

$C_2$–$C_{12}$-Alkylene is, for example, 1,2-ethylene, 1,3-propylene, 1,4-butylene, 1,2-cyclohexylene and 1,2-cyclopentylene.

Aryl is, for example, a carbocyclic aromatic radical having from 6 to 18 framework carbon atoms or a heteroaromatic radical having from 5 to 18 framework carbon atoms, in which no, one, two or three framework carbon atom(s) per ring but at least one framework carbon atom in the overall molecule can be replaced by heteroatoms selected from the group consisting of nitrogen, sulphur and oxygen. Furthermore, the carbocyclic aromatic radicals or heteroaromatic radicals can be substituted by up to five identical or different substituents per ring which are selected from the group consisting of chlorine, fluorine, cyano, $C_1$–$C_{12}$-alkyl, $C_6$–$C_{12}$-aryl, for example phenyl and $C_1$–$C_6$-alkoxy. Examples of carbocyclic aromatic radicals having from 6 to 18 framework carbon atoms are phenyl, naphthyl, phenanthrenyl, anthracenyl and fluorenyl; heteroaromatic radicals having from 5 to 18 framework carbon atoms in which no, one, two or three framework carbon atom(s) per ring but at least one framework carbon atom in the overall molecule can be replaced by heteroatoms selected from the group consisting of nitrogen, sulphur and oxygen are, for example, pyridinyl, oxazolyl, thiophenyl, benzofuranyl, benzothiophenyl, dibenzofuranyl, dibenzothiophenyl, furanyl, indolyl, pyridazinyl, pyrazinyl, pyrimidinyl, thiazolyl, triazolyl or quinolinyl.

Arylalkyl radicals are each, independently of one another, a straight-chain, cyclic, branched or unbranched alkyl radical as defined above which is monosubstituted, polysubstituted or fully substituted by aryl radicals as defined above.

The preferred substitution patterns for compounds of the formula (I) are defined in the following:

$R^1$ and $R^2$ are each preferably, independently of one another, $C_1$–$C_8$-alkyl or $C_5$–$C_{14}$-aryl or are together part of a monocyclic $C_5$–$C_{12}$-alkyl radical.

$R^1$ and $R^2$ are each particularly preferably, independently of one another, more preferably are identical and are each, methyl, phenyl or are together part of a furanylidene, tetrahydronaphthalenylidene or cyclohexylidene radical.

$R^3$ and $R^4$ are each preferably, independently of one another, $C_1$–$C_{12}$-alkyl or $C_5$–$C_{14}$-aryl or the moiety $NR^3R^4$ is a monocyclic $C_4$–$C_{12}$-alkyl radical.

$R^3$ and $R^4$ are each particularly preferably, independently of one another, more preferably are identical and are each, methyl, ethyl, isopropyl or the moiety $NR^3R^4$ is N-morpholinyl, N-methyl-1,4-piperazin-N-yl or prolinyl.

Particularly preferred compounds of the formula (I) are: 2,2-dimethyl-1-fluoro-1-diisopropylaminoethylene, 2,2-cyclohexylidene-1-fluoro-1-piperidinoethylene, 2,2-diphenyl-1-fluorodimethylaminoethylene, 2,2-(3-furanylidene)-1-fluoro-1-diethylaminoethylene and 2,2-(2-tetrahydronaphthalenylidene)-1-fluoro-1-prolinoethylene.

Preferred aprotic tertiary amines are amines of the formulae (IIa) and (IIb),

$NR^5R^6R^7$ (IIa)

$(R^8)_2N$-L-$N(R^8)_2$ (IIb)

where $R^5$, $R^6$ and $R^7$ are each, independently of one another, $C_1$–$C_{12}$-alkyl or [($C_2$–$C_{12}$-alkylene)-O]$_n$($C_1$–$C_{12}$-alkyl)] where n=1 to 5 or two or three of the radicals $R^5$, $R^6$ and/or $R^7$ together with the nitrogen atom form a monocyclic or bicyclic radical having a total of from 3 to 12 or from 5 to 15 carbon atoms, L is $C_2$–$C_6$-alkylene and the radical $R^8$ are each, independently of one another, $C_1$–$C_8$-alkyl or two radicals together form $C_2$–$C_6$-alkylene.

In the formula (IIa), $R^5$, $R^6$ and $R^7$ are each preferably, independently of one another, $C_1$–$C_{12}$-alkyl, and are particularly preferably identical and are each $C_1$–$C_8$-alkyl.

Particularly preferred aprotic tertiary amines are triethylamine, tetramethylethylenediamine and [2.2.2]-1,4-diazabicyclooctane.

Preferred N-heterocyclic compounds are substituted or unsubstituted pyridines and quinolines, with pyridine being particularly preferred.

For the purposes of the invention, the use of triethylamine is very particularly preferred.

The molar ratio of aprotic, tertiary amine or N-heteroaromatic compound to compounds of the formula (I) is, for example and preferably, from 0.1:1 to 20:1, more preferably from 1:1 to 10:1 and particularlypreferably from 1:1 to 5:1.

The molar ratio of hydrogen fluoride to aprotic, tertiary amine or N-heteroaromatic compound is, for example and preferably, from 0.2:1 to 10:1 per nitrogen atom.

The mixtures of the invention comprising compounds of the formula (I), at least one aprotic tertiary amine or at least one N-heteroaromatic compound and hydrogen fluoride can be obtained, for example, by mixing the compounds of the formula (I) with aprotic tertiary amine or N-heteroaromatic compounds and hydrogen fluoride or preferably by mixing the compounds of the formula (I) with mixtures of aprotic, tertiary amine or N-heteroaromatic compound and hydrogen fluoride, which in various compositions such as (NEt$_3$×3 HF) or (pyridine×9HF) are also commercially available.

The compounds of the formula (I) can be prepared particularly advantageously by converting compounds of the formula (III),

(III)

where $R^1$, $R^2$, $R^3$ and $R^4$ are as defined above, including the preferred ranges mentioned, in a step a) into compounds of the formulae (IVa) and (IVb)

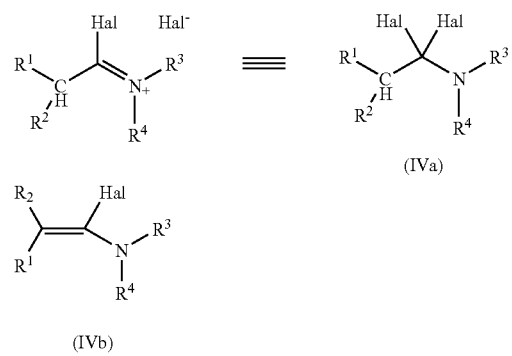

(IVa)

(IVb)

where the radicals Hal are each, independently of one another, chlorine, bromine or fluorine and when Hal is chlorine or bromine, converting the compounds of the formulae (IVa) and (IVb) by means of ionic fluoride into compounds of the formulae (IVa) and (IVb) in which Hal is fluorine in a step b) and in a step c), distilling the compounds of the formulae (IVa) and (IVb) in which Hal is fluorine.

Subsequently, the compounds of the formula (I) can be reacted in a step d) with at least one aprotic tertiary amine or at least one N-heteroaromatic compound and hydrogen fluoride or mixtures of at least one aprotic tertiary amine or N-heteroaromatic compound and hydrogen fluoride to give the mixtures of the invention.

Preferred halogenating agents for step a) are phosphorus pentachloride, phosphorus pentabromide, thionyl chloride, thionyl bromide, phosgene and/or oxalyl chloride, with greater preference being given to phosphorus pentachloride, thionyl chloride, phosgene and/or oxalyl chloride.

The molar ratio of halogenating agent to compound of the formula (III) is, for example and preferably, from 0.9:1 to 10:1, more preferably from 1:1 to 2:1 and particularly preferably from 1.02:1 to 1.5:1.

As the solvent for step a), it is possible to use aliphatic, alicyclic or aromatic, halogenated or unhalogenated hydrocarbons, for example petroleum spirit, benzene, toluene, xylene, chlorobenzene, the isomeric dichlorobenzene, petroleum ether, hexane, cyclohexane, dichloromethane, chloroform, and/or ethers such as diethyl ether, diisopropyl ether, dioxane, tetrahydrofuran or ethylene glycol dimethyl or diethyl ether.

The reaction temperature in step a) can be, for example, from −20° C. to the boiling point of the solvent used at the reaction pressure but is not more than 150° C., preferably from −10° C. to the boiling point of the solvent used at the reaction pressure but not more than 50° C.

The reaction pressure in step a) can be, for example, from 0.8 to 20 bar, preferably from 0.9 to 3 bar, more preferably ambient pressure.

The work-up after the reaction can be carried out, for example, by distilling off all volatile constituents and drying the residue in a high vacuum.

In step b), the compounds of the formula (VI) are reacted with ionic fluoride.

Ionic fluorides are, for example, quaternary ammonium or phosphonium fluorides or alkali metal fluorides or mixtures of the compounds mentioned.

Examples of ammonium or phosphonium fluorides are compounds of the formula (V),

$$(cation^+)(F^-) \quad (V)$$

where (cation$^+$) is a cation of the formula (VI)

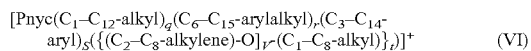

$$[Pnyc(C_1-C_{12}\text{-alkyl})_q(C_6-C_{15}\text{-arylalkyl})_r(C_3-C_{14}\text{-aryl})_s(\{(C_2-C_8\text{-alkylene})-O\}_{t'}(C_1-C_8\text{-alkyl})\}_t)]^+ \quad (VI)$$

where

Pnyc is nitrogen or phosphorus and $(q+r+s+t)=4$.

However, preference is given to using alkali metal fluorides or mixtures of alkali metal fluorides, with particular preference being given to sodium, potassium and caesium fluorides and very particular preference being given to sodium fluoride.

The molar ratio of ionic fluoride to compound of the formula (IVa) or (IVb) used can be, for example, from 0.7 to 5, preferably from 0.9 to 2 and particularly preferably from 1.1 to 1.7. An upper limit on the amount of ionic fluoride which can be used is imposed only by economic considerations.

Step b) is preferably carried out in an organic solvent. Suitable organic solvents are, for example: nitriles such as acetonitrile, propionitrile, benzonitrile, benzyl nitrile or butyronitrile; amides such as N,N-dimethylformamide, N,N-dimethylacetamide, N-methyl-formanilide, N-methylpyrrolidone and dimethylimidazolidinone and also the amides used as starting compounds for the preparation of the compounds of the formula (VI) or sulphoxides such as dimethyl sulphoxide, sulphones such as tetramethylene sulphone, polyethers such as 1,4-dioxane, ethylene glycol dimethyl ether, ethylene glycol diethyl ether, diethylene glycol dimethyl ether, diethylene glycol diethyl ether, benzotrifluoride or mixtures of such organic solvents.

The water content of the solvent used in the process of the invention is preferably not more than 0.2% by weight, more preferably not more than 0.05% by weight. Such a water content is preferably achieved by partial distillation or drying in a manner known per se. When alkali metal fluorides are used, the solvent is particularly preferably simultaneously dried or partly distilled in the presence of the alkali metal fluoride used.

The reaction temperature in step b) can be, for example, from 60° C. to the boiling point of the solvent used at the reaction pressure but not more than 180° C., preferably from 110° C. to the boiling point of the solvent used at the reaction pressure but not more than 150° C.

The reaction pressure can be, for example, from 0.8 to 30 bar, preferably from 1 to 2 bar.

If desired, the reactivity of the ionic fluorides can be modified by means of additives. Suitable additives are, for example, phase transfer catalysts.

Suitable phase transfer catalysts are, for example, crown ethers, such as 18-crown-6, 12-crown-4, dibenzo-18-crown-6 or dibenzo-12-crown-4, cryptands such as cryptand [2.2.2] or podands such as polyglycol ethers or compounds of the formula (VII),

$$(Cation^+)(Anion^-) \quad (VII)$$

where (Cation$^+$) has the abovementioned meanings and preference ranges and (Anion$^-$) is the anion of an organic or inorganic acid.

In step c), the compounds of the formula (I) are obtained in high yield and purity by distillation, preferably at from 0.001 to 800 mbar.

As an alternative to the above-described process for preparing the compounds of the formula (I) or the mixtures of the invention, they can also be prepared by a process which is characterized in that compounds of the formula (III) having the above-described meanings are reacted in the presence of oxalyl fluoride and/or difluorophosgene and, if appropriate, an organic solvent.

As organic solvents, it is possible to use those mentioned above in the same way.

The molar ratio of oxalyl fluoride and/or difluorophosgene to compounds of the formula (I) is then, for example, and preferably, from 0.8:1 to 20:1, more preferably from 1:1 to 2:1 and particularly preferably from 1.02:1 to 1.1:1. The use of larger amounts is possible, but does not result in an improvement in the yield.

The reaction temperature can be, for example, from −50° C. to 100° C., preferably from −10° C. to 50° C.

The reaction pressure can then be, for example, from 0.8 to 20 bar, preferably from 1.5 to 5 bar.

The work-up after the reaction can be carried out, for example, by distilling off all volatile constituents and drying the residue in a high vacuum.

The compounds of the formula (I) are obtained according to the invention in a high yield and purity.

To prepare the mixtures of the invention, step d) can then be carried out as described above.

In a preferred embodiment of this process, the mixtures of the invention are obtained in a one-pot process by reacting the compounds of the formula (III) with oxalyl fluoride and/or difluorophosgene with addition of at least one aprotic tertiary amine or at least one N-heteroaromatic compound and hydrogen fluoride or mixtures of at least one aprotic tertiary amine or at least one N-heteroaromatic compound and hydrogen fluoride.

The addition of aprotic tertiary amine or N-heteroaromatic compound serves partly to react with hydrogen fluoride, and the addition of the mixture of at least one aprotic tertiary amine or N-heteroaromatic compound and hydrogen fluoride serves to set an optimal ratio between compounds of the formula (I), aprotic tertiary amine or N-heteroaromatic compound and hydrogen fluoride.

The compounds of the formula (I) and in particular the mixtures of the invention are particularly useful for the preparation of fluorine compounds from the corresponding hydroxy compounds and for the preparation of geminal difluoro compounds from the corresponding carbonyl compounds.

The invention therefore also encompasses a process for preparing fluorine-containing compounds, which is characterized in that compounds containing hydroxy and/or carbonyl groups are reacted with compounds of the formula (I) and/or the mixtures of the invention.

Preferred compounds containing hydroxy and/or carbonyl groups are compounds which contain at least one aliphatic hydroxy group and/or at least one keto group and/or at least one aldehyde group and/or a carboxyl group.

Particularly preferred compounds containing hydroxy and/or carbonyl groups are compounds which contain an aliphatic hydroxy group or a keto group or an aldehyde group or a carboxyl group.

The fluorine-containing compounds which can be prepared according to the invention are particularly useful for the preparation of pharmaceuticals, agrochemicals and liquid crystals.

The compounds of the formula (I) and mixtures of the invention have the advantage that they are simple to prepare and are storage-stable and make it possible to convert hydroxy and carbonyl compounds into the corresponding fluoro and/or difluoro compounds in high yields. The processes of the invention for preparing the abovementioned compounds and mixtures start out from readily available starting materials and give the products in high yields.

EXAMPLES

Example 1

Preparation of a Fluorination Reagent Comprising 2,2-cyclohexylidene-1-fluoro-1-diisopropylaminoethylene 200 ml of dry dichloromethane were placed in a dry autoclave and 63.3 g of N,N-diisopropylcyclohexanecarboxamide were subsequently added. After the autoclave had been closed, it was cooled to 0° C. and 35 g of oxalyl fluoride was then injected into the solution in small portions while stirring. Stirring was continued for 8 hours at 20° C., the gases were then vented via a scrubber and a mixture of 33 g of triethylamine trishydrofluoride and 10.1 g of triethylamine was then added. After stirring for another hour, the dichloromethane was distilled off under a low vacuum at an internal temperature of 20–25° C.

The reagent can be used without further purification.

Example 2

Reaction of an Alcohol with a Fluorination Reagent Comprising 2,2-cyclohexylidene-1-fluoro-1-diisopropylaminoethylene In a dry polyethylene vessel, a solution of 1.3 g (9.6 mmol) of 1-phenyl-1-propanol in 5 ml of dry dichloromethane was added dropwise under a protective gas atmosphere to a solution of 4.3 g (11.5 mmol) of the mixture from Example 1 having the approximate formula 2,2-cyclohexylidene-1-fluoro-1-diisopropylaminoethylene*triethylamine*3 HF in 10 ml of dry dichloromethane over a period of about 5 minutes. The mixture was stirred at 20° C. for 4 hours. 20 ml of ice water were then added and the aqueous phase was extracted twice with 20 ml each time of dichloromethane. The combined organic phases were dried over sodium sulphate, filtered and concentrated. 1.11 g (8.0 mmol, 84% of theory) of 1-fluoro-1-phenylpropane as a colourless liquid remained as residue.

What is claimed is:
1. Mixtures comprising
compounds of the formula (I),

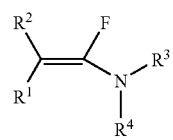

(I)

where
$R^1$ and $R^2$ are each, independently of one another, $C_1$–$C_{12}$-alkyl, $C_1$–$C_{12}$-fluoroalkyl, $C_4$–$C_{15}$-aryl, $C_5$–$C_{16}$-arylalkyl, or $[(C_2$–$C_{12}$-alkylene)-O]$_n$($C_1$–$C_{12}$-alkyl)] where n=1 to 5 or are together part of a cyclic radical having a total of from 3 to 24 carbon atoms and
$R^3$ and $R^4$ are each, independently of one another, $C_1$–$C_{12}$-alkyl, $C_4$–$C_{15}$-arylalkyl or $C_5$–$C_{16}$-aryl or the moiety $NR^3R^4$ is a cyclic amino radical having a total of from 3 to 18 carbon atoms or
$R^1$ and/or $R^2$ and $R^3$ and/or $R^4$ are together part of a cyclic radical having a total of from 4 to 18 carbon atoms,
at least one aprotic, tertiary amine which has no fluorine atoms in the α-position relative to the nitrogen and/or at least one N-heteroaromatic compound and hydrogen fluoride.

2. Mixtures according to claim 1 containing precisely one aprotic, tertiary amine which has no fluorine atoms in the α position relative to the nitrogen.

3. Mixtures according to claim 1, characterized in that, in the formula (I),
$R^1$ and $R^2$ are each, independently of one another, $C_1$–$C_8$-alkyl or $C_5$–$C_{14}$-aryl or are together part of a monocyclic $C_5$–$C_{12}$-alkyl radical.

4. Mixtures according to claim 1, characterized in that, in the formula (I),
$R^1$ and $R^2$ are each, independently of one another, methyl or phenyl or are together part of a furanylidene, tetrahydronaphthalenylidene or cyclohexylidene radical.

5. Mixtures according to claim 1, characterized in that, in the formula (I),
$R^1$ and $R^2$ are identical and are each methyl or phenyl or are together part of a furanylidene, tetrahydronaphthalenylidene or cyclohexylidene radical.

6. Mixtures according to claim 1, characterized in that, in the formula (I),
$R^3$ and $R^4$ are each, independently of one another, $C_1$–$C_{12}$-alkyl or $C_5$–$C_{14}$-aryl or the moiety $NR^3R^4$ is a monocyclic $C_4$–$C_{12}$-alkyl radical.

7. Mixtures according to claim 1, characterized in that, in the formula (I),
$R^3$ and $R^4$ are each, independently of one another, methyl, ethyl or isopropyl or the moiety $N^3R^4$ is N-morpholinyl, N-methyl-1,4-piperazin-N-yl or prolinyl.

8. Mixtures according to claim 1, characterized in that the formula (I) represents 2,2-dimethyl- 1-fluoro-1-diisopropylaminoethylene, 2,2-cyclohexylidene-1-fluoro-1-piperidinoethylene, 2,2-diphenyl-1 -fluorodimethylaminoethylene, 2,2-(3-furanylidene)-1-fluoro-1-diethylaminoethylene or 2,2-(2-tetrahydro-naphthalenylidene)-1-fluoro-1-prolinoethylene.

9. Mixtures according to claims 1, characterized in that aprotic tertiary amines are compounds of the formulae (IIa) and (IIb)

  (IIa)

  (IIb)

where $R^5$, $R^8$ and $R^7$ are each, independently of one another, $C_1$–$C_{12}$-alkyl or $[(C_2$–$C_{12}$-alkylene)-O]$_n$($C_1$–$C_{12}$-alkyl)] where n=1 to 5 or two or three of the radicals $R^5$, $R^6$ and/or $R^7$ together with the nitrogen atom form a monocyclic or bicyclic radical having a total of from 3 to 12 or from 5 to 15 carbon atoms, L is $C_2$–$C_6$-alkylene and the radicals $R^8$ are each, independently of one another, $C_1$–$C_8$-alkyl or two radicals together form $C_2$–$C_6$-alkylene.

10. Mixtures according to claims 1, characterized in that aprotic tertiary amines are triethylamins, tetramethylethylenediamine and [2.2.2]-1,4-diazabicyclooctane.

11. Mixtures according to claims 1, characterized in that the molar ratio of aprotic, tertiary amine or N-heteroaromatic compound to compounds of the formula (I) is from 0.1:1 to 20:1.

12. Mixtures according to claim 1, characterized in that the molar ratio of hydrogen fluoride to aprotic, tertiary amine or N-heteroaromatic compound is from 0.2:1 to 10:1 per nitrogen atom.

13. Process for preparing fluorine-containing compounds, characterized in that compounds containing hydroxyl and/or carbonyl groups are reacted with mixtures according to claim 1.

* * * * *